United States Patent
Polak et al.

(10) Patent No.: US 6,379,622 B1
(45) Date of Patent: Apr. 30, 2002

(54) SENSOR INCORPORATING A QUANTUM DOT AS A REFERENCE

(75) Inventors: Anthony Polak, Lake Zurich; Ji Zhu, Palatine, both of IL (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/832,538

(22) Filed: Apr. 11, 2001

(51) Int. Cl.[7] ................................................ G01N 21/63
(52) U.S. Cl. ............................ 422/82.06; 422/82.07; 422/101; 422/102; 435/7.1; 435/287.2; 435/297.1; 436/518
(58) Field of Search ....................... 422/82.06, 82.07, 422/82.08, 82.09, 82.11, 101; 250/307, 364, 458.1, 440.11, 338.4, 438; 435/7.1; 356/45, 445, 300, 243.1, 243.2, 243.8; 600/317, 341; 436/518

(56) References Cited

U.S. PATENT DOCUMENTS

| | | | |
|---|---|---|---|
| 3,877,784 A | | 4/1975 | Lin |
| 4,058,732 A | | 11/1977 | Wieder |
| 4,150,295 A | | 4/1979 | Wieder |
| 4,344,438 A | | 8/1982 | Schultz |
| 4,737,464 A | | 4/1988 | McConnell et al. |
| 4,791,310 A | | 12/1988 | Honig et al. |
| 4,954,435 A | * | 9/1990 | Krauth et al. ............... 435/7.93 |
| 5,061,076 A | | 10/1991 | Hurley |
| 5,143,066 A | | 9/1992 | Komives et al. |
| 5,496,997 A | | 3/1996 | Pope |
| 5,660,848 A | | 8/1997 | Moo-Young |
| 5,756,115 A | | 5/1998 | Moo-Young |
| 5,814,449 A | | 9/1998 | Schultz et al. |
| 5,871,628 A | | 2/1999 | Dabiri et al. |
| 5,990,479 A | | 11/1999 | Weiss |
| 5,995,860 A | | 11/1999 | Sun et al. |
| 6,002,954 A | | 12/1999 | Van Antwerp et al. |
| 6,011,984 A | | 1/2000 | Van Antwerp et al. |
| 6,110,630 A | | 8/2000 | Reddy et al. |
| 6,114,038 A | * | 9/2000 | Castro et al. .......... 428/402.24 |
| 6,114,350 A | | 9/2000 | Randall et al. |
| 6,121,075 A | * | 9/2000 | Yamashita et al. .......... 438/149 |
| 6,163,714 A | | 12/2000 | Stanley et al. |
| 6,177,684 B1 | | 1/2001 | Sugiyama |
| 6,251,303 B1 | * | 6/2001 | Bawendi et al. ............. 252/301 |
| 6,274,323 B1 | * | 8/2001 | Bruchez et al. ............. 205/307 |

FOREIGN PATENT DOCUMENTS

| | | |
|---|---|---|
| EP | 0761159 A3 B1 | 3/1998 |
| WO | WO 00/20862 | 4/2000 |

OTHER PUBLICATIONS

Sohrab Mansouri and Jerome S. Schultz, "A Miniature Optical Glucose Sensor Based On Affinity Binding", Biotechnology, 1984, pp 885–890.

W. Rudolf Seitz, "Optical Sensors Based In Immobilized Reagents", Biosensors Fundamentals and Applications, Oxford University Press, copyright 1987, pp 599–603.

D. L. Meadows and J. S. Schultz, "Design, Manufacture and Characterization of an Optical Fiber Glucose Affinity Sensor Based on An Homogeneous Fluorescence Energy Transfer Assay System", Analytica Chimica Acta 280, 1993, pp 21–30.

Klaus Mosbach and Olof Ramström, "The Emerging Technique of Molecular Imprinting and Its Future on Biotechnology", Bio/Technogoly vol. 14, 1996, pp 163–170.

Margaret A. Hines et al., Synthesis and Characterization of Strongly Liminescing ZnS–Capped CdSe Nanocrystals, J. Phys. Chem., 100, 1996, pp 468–471.

Dmitri Ivnitski et al., "Biosensors for Detection of Pathogenic Bacteria", Biosensors and Bioelectronics 14, 1999, pp 599–624.

Ryan J. Russell et al., "A Flourescense–Based Glucose Biosensor Using Concanavalin A and Dextran Encapsulated In A Poly(ethylene glycol) Hydrogel", Analytical Chemistry vol. 71, No. 15, 1999, pp 3126–3132.

M. Dittrich et al., "Branched Oligoester Microspheres Fabricated By A Rapid Emulsion Solvent Extraction Method", J. Microencapsulation, vol. 17, No. 5, 2000, pp 587–598.

J. Molpeceres et al., "Biodegradable Nanoparticles As A Delivery System For Cyclosporine: Preparation and Characterization", J. Microencapsulation, vol. 17, No. 5, 2000, pp 599–614.

Ralph Ballerstadt and Jerome S. Schultz, "A Fluorescence Affinity Hollow Fiber Sensor For Continuous Transdermal Glucose Monitoring", Analytical Chemistry vol. 72 No. 17, 2000, pp 4185–4192.

The Nut Factory: Kitchen: Interesting Facts: Chocolate Panning:, "Panning Nuts in Chocolate", <http://www.thenutfactory.com/kitchen/facts/facts–chocolate–panning-.html>, Mar. 16, 2001, pp 1–4.

John Franjione, Ph. D. et al. —Technology Today—Art & Science Microencapsulation, "The Art and Science of Microencapsulation", <http://www.swri.org/3pubs/ttoday/summer/microeng.htm>, Mar. 16, 2002, pp 1–7.

\* cited by examiner

*Primary Examiner*—Christopher L. Chin
*Assistant Examiner*—Gary W. Counts

(57) ABSTRACT

The present invention provides a device and methods for quantitatively detecting the presence of an analyte by referencing the analyte variant signal to an analyte invariant reference signal. The devices contain quantum dots as the invariant references. The reference quantum dots provide a fluorescent signal whose intensity in invariant with respect to the optical signal associated with the analyte concentration. Both the optical path for the analyte specific and invariant reference signal are substantially identical. Therefore, by measuring the intensity ratio of the analyte specific signal to the reference signal, errors associated with optical path length, absorptivity and scattering are eliminated.

30 Claims, 1 Drawing Sheet

SENSOR INCORPORATING A QUANTUM DOT AS A REFERENCE

BACKGROUND OF THE INVENTION

The present invention provides improved devices for detecting the presence of an analyte in a sample. Common optical biological sensor devices use fluorescent labels (throughout this text the term "labeled analogue" refers to an analogue labeled with a fluorescent label) to signal the presence of analyte.

A well know problem associated with fluorescent dyes and optical measurements is that the fluorescent response (intensity) of an optical sensor is dependent on the intensity of the light that irradiates it. The intensity of the light that strikes the optical sensor is in turn dependent upon the optical path length and the absorptivity and scattering of the media that the light must travel through before it reaches the monitoring device, and the path the fluorescent signal must take in order to reach the detector. In addition, any variation in the intensity of the power output of the light emitting device will be interpreted as a change in the concentration of the analyte.

Various approaches have been used to solve this problem. One strategy is to incorporate a separate internal reference dye in the sensor.

The reference dye can be an organic dye, which fluoresces at a substantially different wavelength than the labeled analogue. The excitation wavelength of the reference dye can be the same as the fluorescent label attached to the analogue or different.

By physically moving the light source and photodetector the intensity of the reference dye can be monitored and optimized. Since the reference dye is in close proximity to the labeled analogue, light emitted from the reference dye and labeled analogue travel substantially the same path to the detector, resulting in a similar attenuation due to scattering, absorption and path length. Therefore, by ratioing the labeled analogue intensity to the reference intensity, any effects due to scattering, absorptivity or path length is removed.

Generally, the fluorescent label and the reference dye absorb and emit at wavelengths different for one another. These absorption and emission wavelengths are inherent to a specific dye/label and limit one's choice of absorption and emission wavelengths to the available dyes. The colors or wavelengths emitted by the dyes tend to bleed together, and if two dyes are required for a device, two lasers of different wavelength are generally required (in order to obtain good spectral separation between the emission wavelengths of the reference and analogue dye). Using two lasers is not only unwieldy, but expensive. These limitations mean that, in practice, it is very difficult to use different dyes in the same device.

Quantum dots have none of these shortcomings. Quantum dots are particles that measure only a few nanometers in diameter. They come in a nearly unlimited palette of colors and can be linked to other molecules (such as bio-molecules, including proteins and polynucleotides, glass, and plastic) to adjust their solubility. The emission wavelength of quantum dots can be tuned by varying the size of the nanoparticles and can be used to make a rainbow of colors with white light or a single-color laser. Furthermore, the quantum dots have better photostability than traditional reference dyes.

By incorporating quantum dots into an analyte sensing device, an internal reference for quantitative analysis of an analyte is provided. Upon irradiation with light at an absorption wavelength, the quantum dot emits at a significantly different wavelength. In addition, quantum dots have a broad absorption band, but a fixed emission wavelength, which depends on the composition of the quantum dot and its size. A broad absorption band means that a wide range of wavelengths (colors) can be used to excite the quantum dot, and yet the nanoparticle still emits at the same emission wavelength.

One benefit of placing a reference in close proximity to the fluorescent label is the ability to maximize the emission intensity available from both the labeled analogue and the reference dye. When the analyte sensing device is implanted in a human, and the excitation source or laser is above the skin, the invariant (analyte independent) nature of the reference emission may be used to focus the excitation beam on the device, and to spatially locate the implant to optimize its signal to noise ratio. Greater precision in focusing the excitation beam, allows for a lower analyte emission requirement; therefore, a smaller device is possible. Accurate focusing allows for a smaller sensor device.

BRIEF SUMMARY OF THE INVENTION

In the analyte sensing devices of the present invention, quantum dots are used as a reference to generate an analyte invariant reference emission intensity. This reference, in conjunction with a labeled analogue, can be used to quantitatively determine the amount of analyte in a sample. When irradiated or excited with electromagnetic radiation at a specific wavelength, or a specific range of wavelengths, the quantum dot can emit at a different wavelength than at which it was excited.

DETAILED DESCRIPTION OF THE INVENTION

Figure 1:
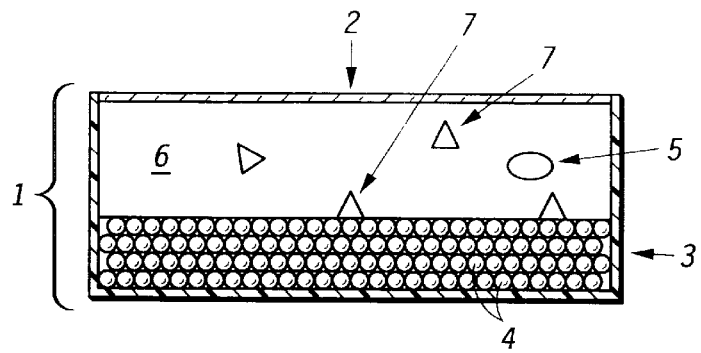
FIG. 1 shows one embodiment of the device of the present invention. The device 1 comprises an analyte-permeable membrane 2 attached to a support 3 to form a chamber. A binding substrate 4 is attached to the support 3, forming a void volume 6. A quantum dot reference 5 is in the void volume 6. A labeled analogue 7 is either associated with the binding substrate 4 or in the void volume 6, depending on the presence of glucose.

The devices and methods for monitoring an analyte in accord with the present invention are based on a competitive reaction for the binding site of the binding substrate between the analyte of interest and a fluorescently-labeled analogue. At low concentrations of analyte, the fluorescently-labeled analogue binds to the binding substrate. As the concentration of analyte increases, the fluorescently-labeled analogue dissociates from the binding substrate. The binding substrate absorbs a majority of the excitation and emission wavelengths of the fluorescent label (e.g., by the action of a dye attached to the binding substrate), such that in the presence of light corresponding to the excitation wavelength, minimum fluorescence is generated when the labeled analogue resides within the binding substrate (i.e., when the concentration of analyte is low). Contrariwise, increased fluorescence is detected when the labeled analogue resides outside the binding substrate (i.e., when the concentration of analyte is high).

The device includes a quantum dot as a reference. By measuring the fluorescence of the labeled analogue in comparison with the emission of the quantum dot, the presence of analyte in the sample can be determined and quantitated.

Due to the smaller Stokes shift (difference between excitation and emission wavelengths) and the inability to readily tune the emission wavelength of organic dyes, a quantum dot reference is a substantial improvement. For pairing with most any fluorescent label, a quantum dot reference may be prepared which will absorb light in the bandwidth of the labeled analogue, but emit at a significantly differently wavelength, thereby allowing a detector to differentiate between the labeled analogue and reference emissions. In this fashion, a quantitative determination of an analyte may be performed by determining the intensity ratio between the label and reference emissions.

Quantum Dot

In the present invention, quantum dots are stable crystals made of semiconductor materials.

The application of quantum dots in a light emitting device is based on the principle that energy band gap increases as the dimension of a material decreases, with subsequent decrease of the emitted wavelength. Because the wavelength of light emitted from a material is dependent on the size of the material, the size of quantum dots may be controlled to obtain emitted light of a desired wavelength.

In a so-called bulk crystal where there is no confinement of carriers, it is well known that the density of state of the carriers increases continuously and parabolically with energy. In a quantum well structure in which carriers are confined one-dimensionally in a crystal, there appear discrete quantum levels. In such a case, the density of state of the carriers changes stepwise.

In a quantum wire structure in which the degree of confinement of the carriers is increased by confinement in two dimensions, the density of states of the carriers in the crystal is modified such that the density of state is a maximum at the bottom edge of each step. Thereby, the sharpness of the spectrum is increased further.

In the present quantum dots, in which the degree of carrier confinement is increased by confinement in three dimensions, the density of states is discrete in correspondence to the discrete quantum levels. A system having such a discrete energy spectrum, in which transition of carriers occurs only discontinuously or stepwise, provides a very sharp spectrum when used for an optical semiconductor device even in a room temperature environment where the carriers experience substantial thermal excitation.

While quantum dots generally absorb electromagnetic radiation over a wide wavelength band (bandwidth) of up to and including 100 nm, they emit at maximum intensity in a relatively narrow wavelength band not exceeding 60 nm, preferably not exceeding 40 nm, and most preferably not exceeding 20 nm, about the center. These bandwidths are determined from measurement of the emission width at ½ of the peak height. The peak emission wavelength of a particular quantum dot is dependent on its composition and physical size.

Generally, the smaller the physical diameter of the particle the smaller the wavelength of the maximum emission. By varying the material and physical diameter of the quantum dot, the emission wavelength of a quantum dot reference can be optimized to not interfere with the emission wavelength of an analyte dependent emission, such as an organic fluorescent label.

Quantum dots, or nanocrystals, in accordance with the present invention have an average cross-section no larger than about 60 Å. Preferably, the quantum dot has an average cross-section of no larger than about 50 Å, more preferably about 1 to 50 Å, even more preferably about 10 to 50 Å.

Quantum dots are generally made from Group II–VI (e.g., MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe) and Group III–V (e.g., GaAs, InGaAs, InP, and InAs) semiconductor compounds that are capable of emitting electromagnetic radiation upon excitation.

Formation of quantum dots from Group III–V and Group II–VI semiconductors is described in U.S. Pat. Nos. 5,251,018; 5,505,928; 5,262,357; and 5,990,479 (incorporated herein by reference). The patents also describe how to control the size of the quantum dots using crystal growth terminators.

The use of Group III–V semiconductor compounds to generate quantum dots has been described (Leonard et al., Appl. Phys. Left. 63(23), 3203 (1993) and Micic et al., Appl. Phys. Left. 68(22), 3150 (1996)).

The use of Group IV semiconductors such as Ge or Si, or organic semiconductors, is also contemplated. For instance, it has been reported that particles of Si and Ge emit a blue light when their size is reduced. By forming quantum dots of these compounds, application in a light emitting device is possible (Kanemitsu et al., Appl. Phys. Lett. 61(18), 2187 (1992) and (Morisaki et al., J. Appl. Phys. 74(4), 2977 (1993)).

In a preferred embodiment, the quantum dots are InP, InAs cores capped with a semiconductor or organic compound (such as TOPO-trioctylphosphine oxide, or dodecylamine) (Guzelian et. al. Appl. Phys. Lett., Vol. 69 (10), p. 1432 (1996), and J. Phys. Chem., Vol. 100, p. 7212 (1996)), or ZnS-capped CdSe (See Hines & Guyot-Sionnest, J. Phys.Chem. 1996, 100, 468).

Figure 2:
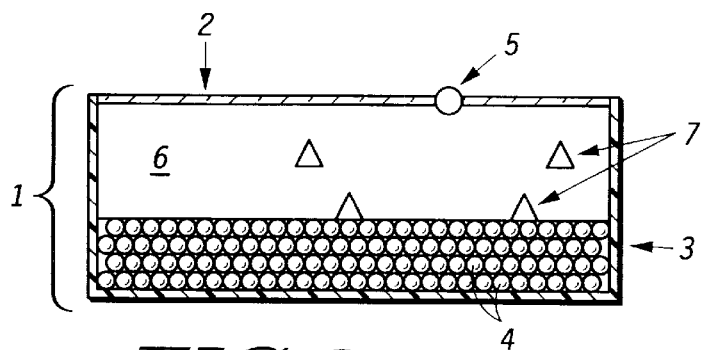
FIG. 2 shows one embodiment of the device of the present invention. The device 1 comprises an analyte-permeable membrane 2 attached to a support 3 to form a chamber. A binding substrate 4 is attached to the support 3, forming a void volume 6. A quantum dot reference 5 is incorporated into the analyte-permeable membrane 2. A labeled analogue 7 is either associated with the binding substrate 4 or in the void volume 6, depending on the presence of glucose.
Figure 3:
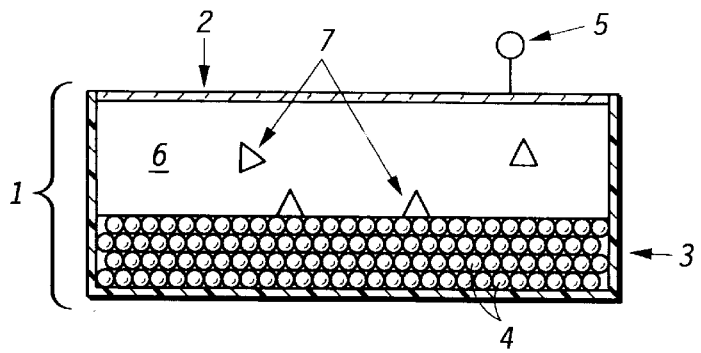
FIG. 3 shows one embodiment of the device of the present invention. The device 1 comprises an analyte-permeable membrane 2 attached to a support 3 to form a chamber. A binding substrate 4 is attached to the support 3, forming a void volume 6. A quantum dot reference 5 is attached onto the analyte-permeable membrane 2. A labeled analogue 7 is either associated with the binding substrate 4 or in the void volume 6, depending on the presence of glucose.
Figure 4:
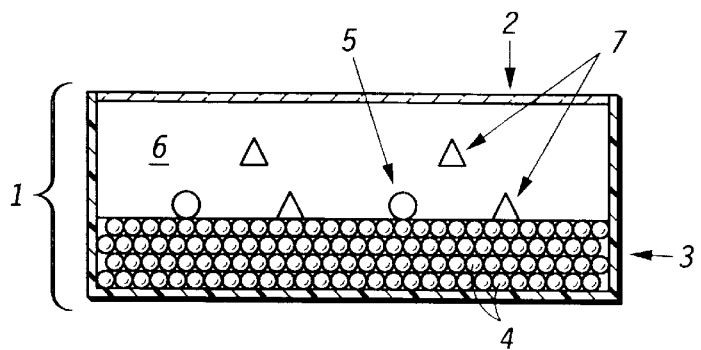
FIG. 4 shows one embodiment of the device of the present invention. The device 1 comprises an analyte-permeable membrane 2 attached to a support 3 to form a chamber. A binding substrate 4 is attached to the support 3, forming a void volume 6. A quantum dot reference 5 is attached onto the binding substrate 4. A labeled analogue 7 is either associated with the binding substrate 4 or in the void volume 6, depending on the presence of glucose.

The quantum dot absorbs at an excitation wavelength and emits at a second wavelength which is detectable outside the body. In one embodiment, the quantum dot or dots are free to float about the void-volume provided between the analyte-permeable membrane and the binding substrate (FIG. 1). In this embodiment, the quantum dots may or may not be associated with a non-analyte specific protein or molecule (e.g., to increase solubility). In a second embodiment, the quantum dot or dots are in the analyte-permeable membrane (FIG. 2). For example, the quantum dots can be incorporated into the analyte-permeable membrane by mixing them with a membrane constituent, such as cellulose acetate, before forming the membrane. In a third embodiment, the quantum dot or dots are covalently bonded to the interior or exterior surface of the analyte-permeable membrane (FIG. 3). In a fourth embodiment, the quantum dot or dots are attached to the binding substrate (FIG. 4). In still another embodiment, the quantum dots can be in more than one location (e.g., attached to both the binding substrate and the analyte-permeable membrane) (not shown). Unlike in other biological implementations, water solubility is not a requirement for the dots.

Unlike the light emitted by the labeled analogue, whose intensity varies with analyte concentration, the intensity of the quantum dot reference emission is invariant. This invariant nature of the reference emission allows for quantification of the label emission. By comparing the intensity of the reference to the labeled emission, quantitative analyte determination is performed.

If the quantum dot reference is in close proximity to the labeled analogue, environmental variations such as skin pigmentation, implant depth, and intensity of the excitation beam are automatically corrected. The invariant reference emission may also be used to optimize the detector position over the device when the device is implanted in a living organism.

For a detector to differentiate between the fluorescent label verses quantum dot reference emissions, the quantum dot preferably emits at least 20 nm, preferably at least 40 nm, and most preferably at least 70 nm longer than the emission from the labeled analog.

Quantum dot reference

Suitable quantum dot references are formed from quantum dots and any carrier that is chemically compatible with the quantum dots and the environment where the reference will be used. Because the quantum dots are disposed on the carder, the carrier should not significantly interfere with the optical performance of the particles. Typical carriers include metal oxides, metal silicates, metal borates, metal phosphates, and plastics, but nonanalyte-specific biomolecules, such as proteins are also possible. Preferably, inert glass (silicon oxide) is used.

In a preferred embodiment, the carrier is silicon oxide glass beads. The beads typically have an average diameter distribution of between about 0.2 to 200 microns, preferably between about 0.2 to 120 microns, and most preferably between about 0.2 to 0.5 microns. Suitable beads may be obtained from CPG, Inc (Lincoln Park, N.J.).

Because the physical size of a quantum dot reference is determined by the size of the carrier, or bead, on which the particles are immobilized, many physical sizes are possible. Quantum dot references may be incorporated into analyte sensing devices in varying ways since their physical size and solubility are readily changed.

The molar ratio of quantum dot references to analogues labeled with fluorochromes should be about 0.01 to 1.0.

Analyte

The present device is useful for making a quantitative determination of one or more analytes in a fluid, such as the interstitial fluid of a living organism. The analyte can be a biologically active molecule or entity, including an enzyme, hormone, peptide, protein, lipid, hapten, antigen, virus, bacteria, and the like. Preferably, the analyte is glucose, coumadin, synthroid, cyclosporin, erythropoietin, lopid, monopril, digoxin, amiodarone, prothrombin, cytokines, chemokines, creatinine, lactate, taxol or fluorouracil. Most preferably the analyte is glucose.

Analyte-Permeable Membrane

The analyte-permeable membrane encloses the components of the device and allows the analyte to enter and exit the device while trapping the device components. That is, the membrane of the present invention can be made of any material impermeable to the labeled analogue, but permeable to the analyte. The membrane is preferably comprised of a biocompatible material. When more than one membrane is present, the materials can be the same or different. Additionally, the analyte-permeable membrane may be coated with at least one substance that promotes biocompatibility, such as polyethylene glycol, an angiogenetic substance, or basic fibroblast growth factor.

Suitable materials include, but are not limited to, cellulose acetate, silicones, fluorosiloxanes, polytetrafluoroethylene (PTFE), polysulfones, polycarbonates, poly(vinyl chlorides), polyamides, ethylene vinyl acetate copolymers, poly(vinylidene) fluoride, poly(urethanes), poly (benzimidazoles), cellulose esters, cellulose triacetate, cellulose, cellulose nitrate, regenerated cellulose, crosslinked poly(vinylpyrrolidone); crosslinked polyacrylamide, and crosslinked poly (hydroxy ethyl methacrylate). More preferably, membranes in accord with the present invention are cellulose acetate.

The thickness of the membrane is preferably between about 10 to 200 microns. More preferably, the thickness is between about 15 to 100 microns. Still more preferably, the thickness is about 20 microns.

The quantum dots may be bound either physically or covalently to the analyte-permeable membrane.

Binding Substrate

The binding substrate has at least one, preferably more than one, affinity binding site for the analyte and labeled analogue to be tested. In a preferred embodiment, the binding substrate has pores, which allow the analyte and labeled analogue to flow into the interior regions of the binding substrate.

The binding substrate may inherently provide a binding site for the analyte and labeled analogue, or a molecule may be attached to the binding substrate to create affinity binding sites on the binding substrate.

Suitable binding substrates may also be made from molecular imprints. Molecular imprints can be formed from polymers and ceramics using the analyte as the mold. Once the analyte is removed, specific binding areas are created. For an overview of molecular imprinting technology, see Mosbach and Ramstrbm, "The Emerging Technique of Molecular Imprinting and its Future Impact on Biotechnology," Biotechnology 14:163–170 (1996).

Dye

Suitable dyes in accordance with the present invention have a broad absorption spectrum that overlaps the fluorescence excitation and emission spectra of the fluorescent label, thereby minimizing fluorescence from the fluorescent label. In such instances, the dyed binding substrate provides a "light-blocking layer" or "light quenching layer" which minimizes or prevents fluorescence from the flourescently-labeled analogue when the concentration of analyte is low.

Preferred dyes include, but are not limited to, Alkali Blue 6B, Azure A, Evans Blue (also called Direct blue 53), and Celestine blue (also called Mordant blue 14). Preferably, the dye is Alkali Blue 6B, which has a broad absorption spectrum from about 500 to 700 nm. Other useful quenching-dyes include Safranin and Pararosaniline.

The dye is linked to the binding substrate, either physically or chemically. Preferably, the dye is covalently linked to the binding substrate. Preferably, the dye is attached to the binding substrate by means of a bifunctional linker. More preferably, the dye is attached using the DVS (i.e., divinyl sulfone) method, as described in *Analytical Chemistry Vol. 72*, No. 17, p. 4186.

Preferably, the binding substrate contains about 3 to 25 mg of dye per mL of a wet suspension of binding substrate. More preferably, the binding substrate contains about 5 to 20 mg/mL. Still more preferably, the binding substrate contains about 10 to 15 mg/mL.

Labeled analogue

"Analogue" refers to one or a plurality of ligands that binds to the binding substrate at low analyte concentrations, and dissociates from the binding substrate as the concentration of analyte increases. "Labeled analogue" refers to an analogue that is fluorescently labeled. This label can be an organic dye or quantum dot.

In the absence of analyte, labeled analogues mostly reside within the pores of the binding substrate. The labeled analogues affinity bind to the binding substrate, but may also affinity bind to the analyte. When analyte flows into the device, it displaces labeled analogues from the binding substrate. Following displacement, the labeled analogues migrate to the void-volume, at which point their emission wavelength can be detected upon excitation. As the concentration of analyte increases within the analyte-permeable membrane package, a greater percentage of the labeled analogues reside in the void-volume; thereby increasing the intensity of labeled analogue's emission.

In certain embodiments, the labeled analogue can also bind, by affinity binding, to the analyte in addition to binding to the binding substrate. The labeled analogue can be any molecule that is too large to pass through the analyte-permeable membrane, but small enough to enter the binding substrate and affinity bind to the analyte or binding substrate. Preferred analogues are Concanavalin-A or dextran.

Attached to the analogue by a covalent bond or other means is a fluorescent label. When irradiated with an appropriate excitation wavelength, the label emits light at a first wavelength which may be detected outside of the body. Although the excitation wavelength is preferably generated by a visible or infrared laser, any suitable electromagnetic radiation from X-ray to infrared may be used. Light and electromagnetic radiation from X-ray to infrared are synonymous as used herein.

The fluorescent label can be any label that fluoresces when irradiated. A broad variety of fluorescent labels are known in the art and are commercially available, for example, from Molecular Probes, and Pharmacia.

Suitable fluorescent labels include those sold under the tradename ALEXA FLUOR™ (Molecular Probes, Eugene, Oreg., USA), Cy5 (AmershamPharmacia, Piscataway, N.J.), and Cy5.5 (AmershamPharmacia, Piscataway, N.J.).

Especially preferred dyes include the ALEXA FLUOR™ dyes, especially ALEXA™ 633, which has an excitation wavelength of 633 nm, and an emission wavelength of 647 nm.

Support

Optionally, the binding substrate may be attached to a support. Suitable supports in accordance with the present invention include silicones; fluorosiloxanes; epoxies; acrylate derivatives, such as methyl methacrylate; polyamides; polyimides; ceramics, such as silica, silicon oxide, and porous silica; and halogenated hydrocarbons, such as PVC and PTFE. Additionally the support can be dextran, compounds with a glucose moiety, a metal oxide, metal silicate, metal borate, metal phosphate, or plastic, such as a bead.

Device

In one preferred embodiment, the device for monitoring an analyte of the present invention includes (a) a support having an interior surface and an exterior surface; (b) a binding substrate comprising a dye, wherein the binding substrate is connected to the interior surface of the support; (c) a spacer connected to the interior surface of the support; (d) an analogue comprising a fluorescent label, wherein the labeled analogue binds reversibly to the binding substrate; and (e) a first membrane having an interior surface and an exterior surface, wherein the interior surface is connected to the spacer.

In addition to being permeable to the analyte and impermeable to the labeled analogue, the first membrane is substantially transparent to each of an excitation wavelength and an emission wavelength of the fluorescent label. The dye absorbs a majority of the excitation and emission wavelengths of the fluorescent label, when the labeled analog affinity binds to the binding substrate. A chamber which encloses the binding substrate and the analogue is defined by the interior surface of the support, the spacer, and the interior surface of the first membrane. The spacer exceeds the binding substrate in elevation such that a void volume exists between the interior surface of the first membrane and the binding substrate. The quantum dot reference can be located in the void volume, attached to the analyte permeable membrane, attached to the analogue, attached to the binding substrate, attached to the spacer, or attached to the support.

In another embodiment the device comprises (a) a core comprising (i) a binding substrate with a binding site for the analyte and labeled analogue; (ii) an analogue that weakly binds in the binding site and that has a label with a first emission wavelength; (iii) a dye that is bound to the binding substrate and that absorbs the first wavelength light; (b) a void volume surrounding the core which contains a reference with a different emission wavelength than the labeled analogue; and (c) an analyte-permeable membrane that encapsulates components (a) and (b) and that is transparent to light of the wavelengths that the labeled analogue and the reference are excited at and emit at.

Excitation Sources and Detectors

Many excitation sources which produce light at the absorption wavelengths of the quantum dot reference and fluorescent label are available. Some possibilities include lasers and LED's. Visible, and infrared lasers, are preferred when the device is implanted in a human because skin is transparent to red and infrared light. A laser emitting between about 630 to 1200 nm, inclusive, is preferred since skin is substantially transparent within these wavelengths.

In a preferred embodiment the optical sensor described in co-pending U.S. patent application Ser. No. 09/832,521, entitled "System Using A Portable Detection Device For Detection of an Analyte Through Body Tissue", filed concurrently with this application, is used.

Many detection systems, including photodiodes, avalanche photodiodes, CCD's, and photomultipliers may be used. In one embodiment, a photodiode detector capable of detecting the 647 nm emission of the labeled analogue and the 750 nm emission of the quantum dot is preferred for a glucose monitor.

A well know problem associated with fluorescent dyes and optical measurements is that the fluorescent response (intensity) of an optical sensor is dependent on the intensity of the light that irradiates it. The intensity of the light that strikes the optical sensor is in turn dependent upon the optical path length, absorptivity and scattering of the media that the light must travel through before it reaches the sensing device, and the path the fluorescent signal must take in order to reach the detector. In addition, any variation in the intensity of the power output of the light emitting device will be interpreted as a change in the concentration of the analyte.

Calibration of the emission signal of the fluorescent label may be effected by ratioing it to that of the reference. Optimization of the emission signal of the fluorescent dye may also be obtained by maximizing the emission intensity of the reference. This results in an optimization of the signal to noise ratio, and a signal which is invariant to optical path length, scattering and absorptivity. Thus, the fluorescent label and reference may be irradiated with light of a specific wavelength, more than one specific wavelength, or a range of wavelengths, which may or may not be the wavelength of maximum absorption. The fluorescence emission may be measured at specific wavelengths, which may or may not be the wavelength of maximum emission intensity, or a range of wavelengths in conjunction with specific light filtering devices.

By this procedure, the fluorescence emission of the fluorescent label may be discerned from that of the reference. Expressing the emission of the fluorescent label as a fraction of the emission of the reference yields a signal ratio that is sensitive to the analyte of interest and less sensitive to the effects of misalignment of the excitation source/detector, the analyte sensing device, and to power fluctuations of the light emitting source of the present invention. This results in improved accuracy, and a prolonged useful life of the sensor.

EXAMPLES

Example 1

Physical Attachment

Quantum dots can be physically attached to a polymer by forming a polymer blend of quantum dots and a polymer using a common solvent.

Using the method described in Hines & Guyot-Sionnest, J. Phys. Chem. 1996, Vol. 100, p. 468, quantum dots were fabricated and dissolved in $CHCl_3$. To 0.5 mL of the quantum dot solution made above was added a solution of 0.214 g of poly(methylmethacrylate) (PMMA) in 1.5 mL of $CHCl_3$. The solution was thoroughly mixed by ultrasonication for 15 minutes and cast onto a glass container. The $CHCl_3$ was allowed to evaporate, leaving a PMMA film with quantum dots physically trapped within the film. The film was then removed from the glass container.

Example 2

Covalent attachment of quantum dots to a cellulose acetate membrane:

Cellulose acetate membranes have residual unesterfied hydroxyl group pendant on the surface, and these free hydroxyl group can be covalently coupled to reactive ligands attached to the quantum dot.

Quantum dots with CdSe cores and ZnS shells will be exposed with large excess 11-mercaptoundecanoic acid and t-butoxide to prepare capping groups with terminal carboxylate group. (See Bawendi, Mikulec & Lee, Patent: WO 00/17656). The carboxylate group pending on the surface of the quantum dots will then be activated by reacting with EDC and N-hydroxylsuccinimide sequentially to form a stable ester functionality with the hydroxyl group of the cellulose acetate.

Example 3

Quantum dot references having an average emission bandwidth in the 750 nm range can be prepared following the procedure of Guzelian et. al. (Appl. Phys. Lett., Vol. 69 (10), p. 1432 (1996), and J. Phys. Chem., Vol. 100, p. 7212 (1996). The nanocrystal compounds were composed of InAs and InP, depending on the desired emission wavelength.

Briefly, the synthesis of InP nanocrystals involves the reaction of $InCl_3$ with TOPO to form an In-TOPO complex followed by the addition of $P(Si(CH_3)_3)_3$, the mixture is then maintained at 100° C. for 3 hours. The temperature is then raised to 265° C. for 6 days. To add a capping molecule, the solution is cooled to 100° C. and a quantity of the desired capping molecule is added (for instance dodecylamine). Quantum dots that are used as a reference need not be water soluble, so further chemical modification is not necessary. However, various functional groups can be attached to the quantum dot, for instance thiols (e.g. dihydrolipoic acid) various mercapto-acid (e.g. mercapto-propionic acid, or mercapto-undecanoic acid) which will allow them to be covalently attached to the membrane/surface of the analyte sensing device. Quantum dots can also be attached to glass beads by reacting a solution of quantum dots, which have carboxylic end group, with amine activated glass beads (for instance, beads purchased from CPG, Lincoln Park, N.J., product # AMP01400A).

Example 4

Preparation of Device

Quantum dots were made by the procedure outlined in Example 1, and dissolved in $CHCl_3$. A viscous solution of a transparent polymer was then made, specifically a solution of polystyrene (MW=280K) in $CHCl_3$ (0.3 g of polystyrene to 1.0 mL $CHCl_3$) was made, to which the quantum dot solution was added. The volume ratio of polymer solution to quantum dot solution was about 0.5:1.0. The resulting solution was then untrasonicated for 15 minutes and the solution poured into a glass beaker and the $CHCl_3$ allowed to evaporate overnight. The resulting sheet contained quantum dots entrapped in a polymer matrix. This rigid structure can then be made into the spacer support structure describer earlier.

What is claimed is:

1. A device for detecting the presence of analyte in a sample, comprising:
    (a) a binding substrate that has at least one affinity binding site for the analyte and a labeled analogue;
    (b) said labeled analogue comprising an analogue and a label, wherein the label emits light at a first wavelength when irradiated;
    (c) a dye bound to the binding substrate, which has an absorption spectrum that overlaps a fluorescence excitation and emission spectra of the label;
    (d) a first reference comprising quantum dots that emit light at a second wavelength when irradiated;
    (e) an analyte-permeable membrane that encapsulates components (a), (b), (c), and (d); and
    (f) a void volume exterior to the binding substrate and interior to the analyte-permeable membrane.

2. The device of claim 1, wherein the binding substrate is attached to a support.

3. The device of claim 1, wherein the quantum dot reference is in the analyte-permeable membrane.

4. The device of claim 1, wherein the quantum dot reference is bonded to a surface of the analyte-permeable membrane.

5. The device of claim 1, wherein the quantum dot reference is covalently attached to the analyte-permeable membrane.

6. The device of claim 1, wherein the quantum dot reference is attached to the binding substrate.

7. The device of claim 1, wherein the void volume is formed by a spacer between the analyte permeable membrane and the binding substrate.

8. The device of claim 7, wherein the quantum dot reference is attached to the spacer.

9. The device of claim 1, wherein the quantum dots comprise at least one Group II–VI semiconductor compound, Group III–V semiconductor compound, or organic semiconductor compound.

10. The device of claim 1, wherein the quantum dots comprise at least one semiconductor compound selected from the group consisting of MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, HgTe, GaAs, InGaAs, InP, InAs, Ge, and Si.

11. The device of claim 1, wherein the quantum dots have an average cross-section no larger than about 60 Å.

12. The device of claim 1, wherein the quantum dots have an average cross-section no larger than about 50 Å.

13. The device of claim 1, wherein the quantum dots have an average cross-section of about 1 to 50 Å.

14. The device of claim 1, wherein the quantum dots have an average cross-section of about 10 to 50 Å.

15. The device of claim 1, wherein the analyte is selected from the group consisting of glucose, coumadin, synthroid, cyclosporin, erythropoietin, lopid, monopril, digoxin, amiodarone, prothrombin, cytokines, chemokines, creatinine, lactate, taxol, and fluorouracil.

16. The device of claim 1, wherein the analyte is glucose.

17. The device of claim 16, wherein the analyte-permeable membrane is cellulose acetate.

18. The device of claim 16, wherein the analogue is Concanavalin-A.

19. The device of claim 16, wherein the label is ALEXA™ 633.

20. The device of claim 1, wherein the analyte-permeable membrane is selected from the group consisting of cellulose acetate, polysulfones, polycarbonates, poly(vinyl chlorides), polyamides, ethylene vinyl acetate copolymers, poly(vinylidene) fluoride, poly(urethanes), poly(benzimidazoles), cellulose esters, cellulose triacetate, cellulose, cellulose nitrate, regenerated cellulose, cross-linked poly(vinylpyrrolidone); crosslinked polyacrylamide, crosslinked poly (hydroxy ethyl methacrylate), silicones, fluorosiloxanes, and polytetrafluoroethylene or combinations thereof.

21. The device of claim 20, wherein the analyte-permeable membrane is coated with at least one substance that promotes biocompatibility.

22. The device of claim 21, wherein the analyte-permeable membrane is coated with polyethylene glycol or an angiogenic substance.

23. The device of claim 21, wherein the analyte-permeable membrane is coated with basic fibroblast growth factor.

24. The device of claim 1, wherein the analogue is Concanavalin-A or dextran.

25. The device of claim 1, comprising more than one labeled analogue.

26. The device of claim 2, wherein the support is dextran, compounds with a glucose moiety, a metal oxide, metal silicate, metal borate, metal phosphate, or plastic.

27. The device of claim 2, wherein the support is a silicon oxide.

28. The device of claim 1, wherein the support is a bead.

29. A method of quantitatively determining the amount of at least one analyte in a sample, which comprises the steps of:
  (a) contacting a sample with the device of claim 1,
  (b) irradiating the device with light,
  (c) determining the intensity of emission from the labeled analogue,
  (d) determining the intensity of emission from the quantum dot reference,
  (e) correlating the intensity of emission from (c) and (d) to thereby determine the amount of analyte in the sample.

30. A method of optimizing the signal to noise ratio of an optical sensor, which comprises the steps of:
  (a) contacting a sample with the device of claim 1,
  (b) irradiating the device with light,
  (c) maximizing the labeled analogue signal/noise ratio by optimizing the reference signal intensity by physically moving the excitation source and detector relative to the sensing device.

* * * * *